United States Patent
Wen

(10) Patent No.: US 10,813,726 B2
(45) Date of Patent: Oct. 27, 2020

(54) PERIOSTEAL ELEVATOR HAVING HOOK-SHAPED COMBLIKE STRUCTURE

(71) Applicant: Shih-Cheng Wen, New Taipei (TW)

(72) Inventor: Shih-Cheng Wen, New Taipei (TW)

( * ) Notice: Subject to any disclaimer, the term of this patent is extended or adjusted under 35 U.S.C. 154(b) by 276 days.

(21) Appl. No.: 15/955,067

(22) Filed: Apr. 17, 2018

(65) Prior Publication Data

US 2019/0247155 A1 Aug. 15, 2019

(30) Foreign Application Priority Data

Feb. 9, 2018 (TW) .............................. 107202064 U

(51) Int. Cl.
 *A61C 8/00* (2006.01)
 *A61C 3/00* (2006.01)
 *A61B 17/32* (2006.01)

(52) U.S. Cl.
 CPC ............ *A61C 8/0089* (2013.01); *A61B 17/32* (2013.01); *A61C 3/00* (2013.01); *A61B 2017/320008* (2013.01)

(58) Field of Classification Search
 CPC ......... A61C 8/0089; A61C 3/00; A61B 17/32; A61B 2017/320008
 USPC ....................................................... 433/144
 See application file for complete search history.

(56) References Cited

U.S. PATENT DOCUMENTS

| | | | | |
|---|---|---|---|---|
| 9,526,517 B2* | 12/2016 | Onuma | ............... | A61B 17/025 |
| 2013/0017509 A1* | 1/2013 | Gordon | ................ | A61B 13/00 |
| | | | | 433/93 |
| 2013/0288196 A1* | 10/2013 | Gordon | .................... | A61C 1/12 |
| | | | | 433/93 |
| 2015/0024339 A1* | 1/2015 | Calderon | ............... | A61C 19/04 |
| | | | | 433/72 |
| 2016/0135921 A1* | 5/2016 | Gordon | .................... | A61C 1/12 |
| | | | | 433/140 |
| 2016/0143648 A1* | 5/2016 | Onuma | .............. | A61B 17/1604 |
| | | | | 606/79 |
| 2017/0296308 A1* | 10/2017 | Lee | ....................... | A61F 2/2803 |
| 2017/0319298 A1* | 11/2017 | Lee | ...................... | A61C 8/0089 |
| 2018/0125622 A1* | 5/2018 | Almoumen | ........ | A61C 17/0202 |

* cited by examiner

*Primary Examiner* — Matthew M Nelson
(74) *Attorney, Agent, or Firm* — Muncy, Geissler, Olds & Lowe, P.C.

(57) ABSTRACT

A periosteal elevator applied to comb and elongate a subcutaneous fibrous tissue includes a stem bar, a first spoon end, and a plurality of hook-shaped comblike structures separated to each other. The first spoon end, fixed to a first end portion of the stem bar, further has a spoon-end edge. The plurality of hook-shaped comblike structures, fixed to the spoon-end edge, further have an extension portion and a hook-like comb portion. The extension portion is extended from the spoon-end edge, and the hook-like comb portion is extended from the extension portion. When the subcutaneous fibrous tissue is cut and separated from a bone tissue, the plurality of hook-shaped comblike structures can comb and elongate the subcutaneous fibrous tissue. In addition, a comb surface of the hook-like comb portion and an inner-side extension surface of the extension portion are together to form an angle within a range of 60 and 100 degrees.

9 Claims, 12 Drawing Sheets

PERIOSTEAL ELEVATOR HAVING HOOK-SHAPED COMBLIKE STRUCTURE

This application claims the benefit of Taiwan Patent Application Serial No. 107202064, filed on Feb. 9, 2018, the subject matter of which is incorporated herein by reference.

BACKGROUND OF THE INVENTION

1. Field of the Invention

The invention relates to a periosteal elevator, and more particularly to a periosteal elevator that has a hook-shaped comblike structure.

2. Description of the Prior Art

With the progress of medical technology, various medical achievements have been successfully and widely provided to ordinary people. In particular, some of these achievements have made some impossible things happen, like cosmetic surgeries, full-mouth dental implants and so on.

In a bone healing study performed by Dr. Branemark, a Sweden orthopedist, in 1955, it was found accidentally that biocompatibility of human bone tissues and/or soft tissues to titanium (Ti) was excellent. Namely, these human tissues can bind with Ti stably. Accordingly, Dr. Branemark and oral surgeons cooperated to develop historically the first dental implant in 1965. Such an innovation did initiate a new era in dental technology, and thus a thriving dental implantation industry in dental history.

Please refer to FIG. 1 and FIG. 2; where FIG. 1 is a schematic cross-sectional view of a wound on an alveolar bone to be implanted in the art, and FIG. 2 demonstrates another state of FIG. 1 having a dental implant in the alveolar bone and with bone grafts filled in the wound.

Herein, the wound is directed to a necessary opening purposely made by cutting in a dental operation. As shown, when a patient needs an implantation operation, it implies that the original tooth grown from this alveolar bone PA21 is already gone, naturally or by human forcing. After the tooth is gone, neighboring bone cells would grow automatically to fill the corresponding alveolus. However, atrophy of the alveolar bone PA21 and the relative gums would be inevitable. Thus, in the art, the implant surgery for implanting a dental implant PA3 into patient's alveolar bone PA21 is an important part of the dental surgeries. In a typical implant surgery, a dentist would firstly apply a surgerical knife or the like cutting tool to cut the subcutaneous fibrous tissue (including PA22a and PA22b) wrapped on the alveolar bone PA21, and then a conventional periosteal elevator PA1 to separate the cut subcutaneous fibrous tissue from the alveolar bone PA21 into two subcutaneous fibrous tissues PA22a and PA22b.

The subcutaneous fibrous tissues PA22a and PA22b include individually periostea PA221a and PA221b, respectively. While the dentist performs cutting to form the separated subcutaneous fibrous tissues PA22a and PA22b from the alveolar bone PA21, the periostea PA221a and PA221b are also separated from the alveolar bone PA21 so as to expose part of the alveolar bone PA21. Thus, the dentist can implant a dental implant PA3 into the alveolar bone PA21, and then feed some bone grafts PA4 onto the alveolar bone PA21, such that the antropic alveolar bone PA21 and gums can be better supported. In the art, the technique of implanting the dental implant PA3 into the alveolar bone PA21 is already common in the dental industry, and thus details thereabout would be omitted herein.

After completing the foregoing operations, the dentist can then suture the separated subcutaneous fibrous tissues PA22a and PA22b. However, since the alveolar bone PA21 embedded with the dental implant PA3 is surrounded and thus supported by the bone grafts PA4, the wound would be slightly bumped due to the aforesaid dental implantation. Therefore, satisfied suturing between the subcutaneous fibrous tissue PA22a and PA22b would be hard to achieve without any further treatment upon the wound.

Refer also to FIG. 3 and FIG. 3A; where FIG. 3 demonstrates a further state of FIG. 2 with cuts at the subcutaneous fibrous tissues of the wound, and FIG. 3A is a schematic perspective view of an enlarged subcutaneous fibrous tissue of the would of FIG. 3. As shown, in order to smooth out the suturing between the subcutaneous fibrous tissues PA22a and PA22b, the dentist would apply a cutting tool (a surgerical knife for example) to make a plurality of cuts at respective inner sides of the subcutaneous fibrous tissues PA22a and PA22b (four cuts shown in FIG. 3, with two thereof labeled as PA220a and PA220b, respectively). The cuts PA220a and PA220b are extended perpendicular to the grain of fibers in the subcutaneous fibrous tissues PA22a and PA22b, respectively. Namely, the cuts PA220a and PA220b are to break corresponding fibers in the subcutaneous fibrous tissues PA22a and PA22b, respectively.

Referring now to FIG. 4, a further state of FIG. 3 with the wound been sutured is schematically demonstrated. As shown, after the inner sides of the corresponding subcutaneous fibrous tissues PA22a and PA22b are cut to form a plurality of cuts PA220a and PA220b, the subcutaneous fibrous tissues PA22a and PA22b can be thus pulled individually to a state that the subcutaneous fibrous tissues PA22a and PA22b can be sutured without bean teared off. Then, stitches PA5 are applied to integrate the subcutaneous fibrous tissues PA22a and PA22b so as to complete the implantation operation.

In the aforesaid operation, after the dental implant PA3 is embedded into the alveolar bone PA21, a plurality of cuts PA220a and PA220b at the inner sides of the subcutaneous fibrous tissues PA22a and PA22b are necessary, and thus the subcutaneous fibrous tissues PA22a and PA22b can be stretched to complete the suturing by the stitches PA5. Such a move to reduce the tension by providing inner cuts PA220a and PA220b to the subcutaneous fibrous tissues PA22a and PA22b, respectively, is ordinary seen in a typical surgery (usually called as a relaxation suturing technique). Here, the conventional periosteal elevator PA1 is simply used to lift the subcutaneous fibrous tissues PA22a and PA22b away from the alveolar bone PA21. It shall be noted that, prior to the suturing, another tool shall be used to perform the necessary tension reduction. In the art, the conventional relaxation suturing technique is performed by cutting off part of subcutaneous fibers so as able to stretch easily the subcutaneous fibrous tissues PA22a and PA22b. However, breeding upon cutting the subcutaneous fibers is inevitable. Also, in some particular situations, numbers and depths of the cuts shall be increased to fulfill the increase in required stretching lengths of the subcutaneous fibrous tissues PA22a and PA22b targeted for a satisfied suturing. Under such a circumstance, additional cuts to the subcutaneous fibrous tissues PA22a and PA22b would be inevitable. While in performing the inner cuts PA220a and PA220b, especially with additional depths, it is quite possible that corresponding dermis (not shown in the figure) would be hurt, and even worse swelling and/or contaminations at the cuts might be possible. Thereupon, postoperative recovery may be prolonged.

SUMMARY OF THE INVENTION

In view of the art and problems described above, possible swelling and/or contaminations may be met after the relaxation suturing by breaking part of the subcutaneous fibers so as to obtain additional length totally for the subcutaneous fibrous tissues, and further the conventional periosteal elevator can only serve a unique function but providing no help for the following relaxation suturing. Accordingly, it is an object of the present invention to provide an improved periosteal elevator that includes a hook-shaped comblike structure to comb and elongate (elongate by combing) the subcutaneous fibers so as to provide longer stretchable lengths for the subcutaneous fibrous tissues.

In the present invention, the periosteal elevator having a hook-shaped comblike structure, applied to comb and elongate a subcutaneous fibrous tissue, includes a stem bar, a first spoon end, and a plurality of hook-shaped comblike structures separated to each other.

The first spoon end, fixed to a first end portion of the stem bar, further has a spoon-end edge.

The plurality of hook-shaped comblike structures, separated to each other and fixed to the spoon-end edge, further have an extension portion and a hook-like comb portion. The extension portion is extended from the spoon-end edge, and the hook-like comb portion is extended from the extension portion. When the subcutaneous fibrous tissue is cut and separated from a bone tissue, the plurality of hook-shaped comblike structures can comb and elongate the subcutaneous fibrous tissue.

In addition, a comb surface of the hook-like comb portion and an inner-side extension surface of the extension portion are together to form an angle within a range of 60 and 100 degrees.

In one embodiment of the present invention, the periosteal elevator further includes a knife protrusion fixed to a spoon-end lateral side of the first spoon end.

In one embodiment of the present invention, the periosteal elevator further includes a second spoon end connected with a second end portion of the stem bar by opposing to the first end portion. The second spoon end is to tear the subcutaneous fibrous tissue off the bone tissue.

In one embodiment of the present invention, the stem bar further has a hand-gripped portion.

In one embodiment of the present invention, the spoon-end edge is one of an arc edge and a straight edge.

In one embodiment of the present invention, neighboring two of the plurality of hook-shaped comblike structures are separated by a predetermined spacing.

In one embodiment of the present invention, the first spoon end has a spoon-end width within a range of 3 mm and 15 mm.

In one embodiment of the present invention, the plurality of hook-shaped comblike structures have a protrusive height within a range of 0.8 mm and 1 mm.

In one embodiment of the present invention, the first spoon end has a spoon-end thickness within a range of 1 mm and 2 mm.

In one embodiment of the present invention, the comb surface of the plurality of hook-shaped comblike structures has a comb-tooth length within a range of 0.1 mm and 0.3 mm.

As stated above, by providing the periosteal elevator having a hook-shaped comblike structure of the present invention, the hook-shaped comblike structures are used to comb and elongate the subcutaneous fibers so as to extend a length of the subcutaneous fibrous tissue. Thereupon, a following suturing process can be benefited and performed with or without a cut, and the risk of swelling and contamination at the wounds or cuts can be substantially reduced.

All these objects are achieved by the periosteal elevator having a hook-shaped comblike structure described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a periosteal elevator having a hook-shaped comblike structure. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention-.invention.

Figure 1:
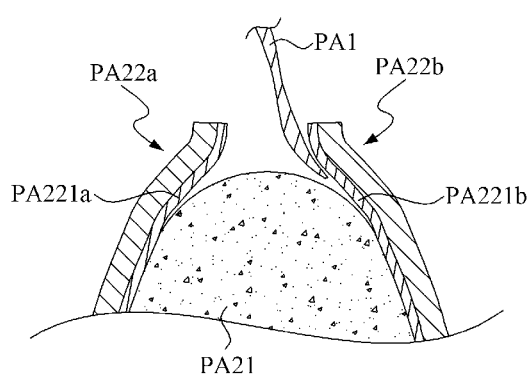
FIG. 1 is a schematic cross-sectional view of a wound on an alveolar bone to be implanted in the art.
Figure 2:
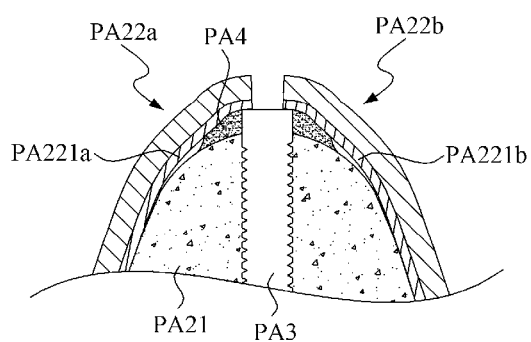
FIG. 2 demonstrates another state of FIG. 1 having a dental implant in the alveolar bone and with bone grafts filled in the wound.
Figure 3:
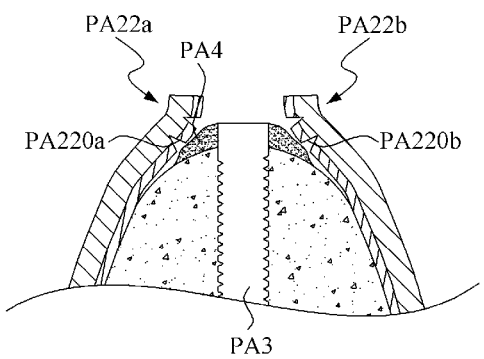
FIG. 3 demonstrates a further state of FIG. 2 with cuts at the subcutaneous fibrous tissues of the wound.
Figure 3A:
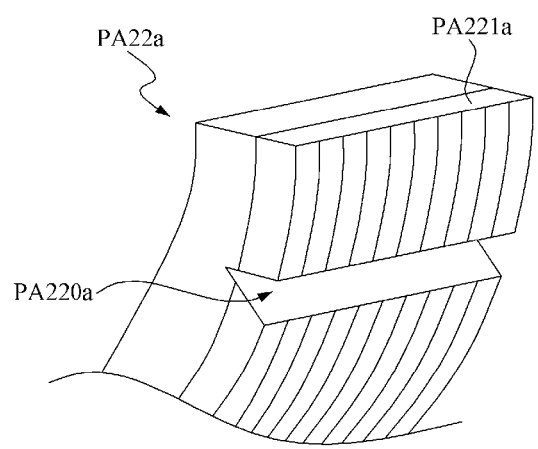
FIG. 3A is a schematic perspective view of an enlarged subcutaneous fibrous tissue of the would of FIG. 3.
Figure 4:
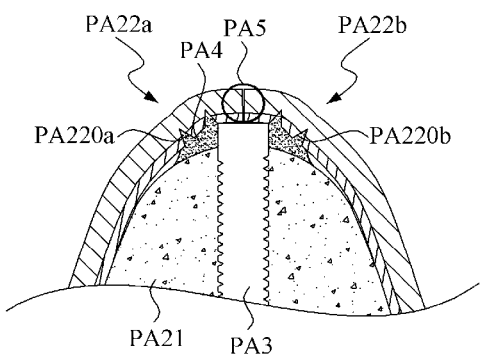
FIG. 4 demonstrates a further state of FIG. 3 with the wound been sutured.
Figure 5:
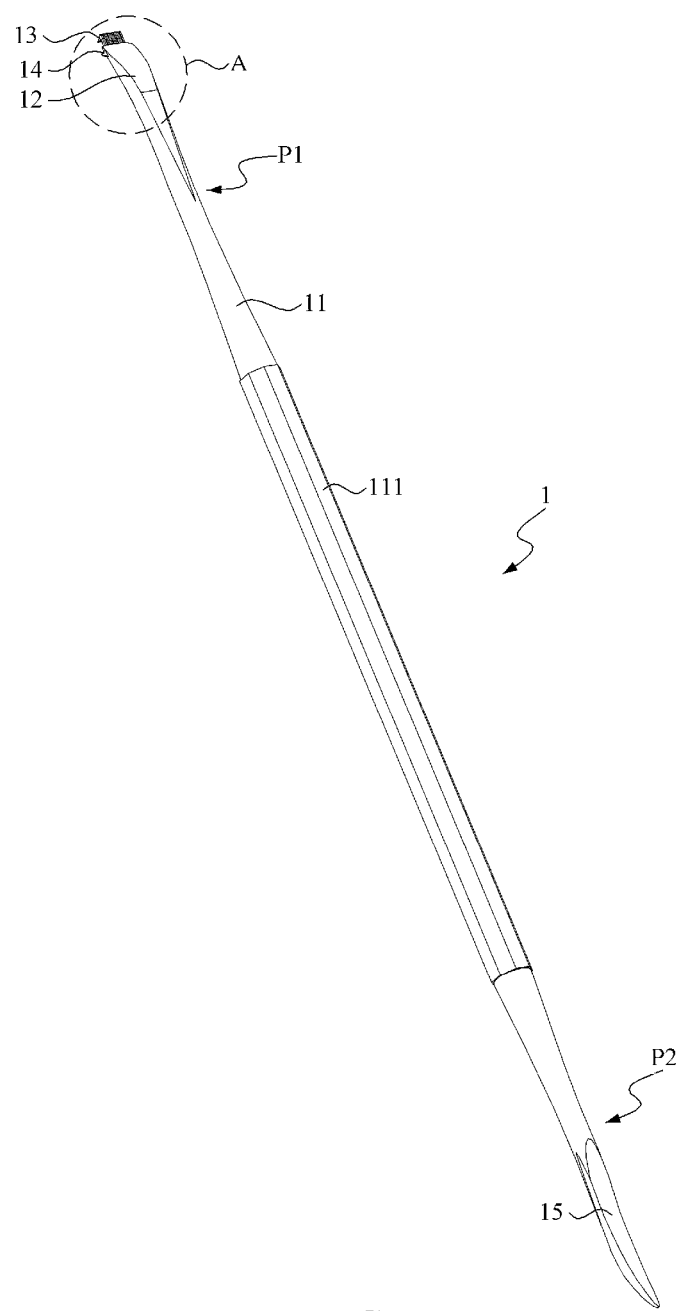
FIG. 5 is a schematic perspective view of a preferred periosteal elevator having a hook-shaped comblike structure in accordance with the present invention.
Figure 6:
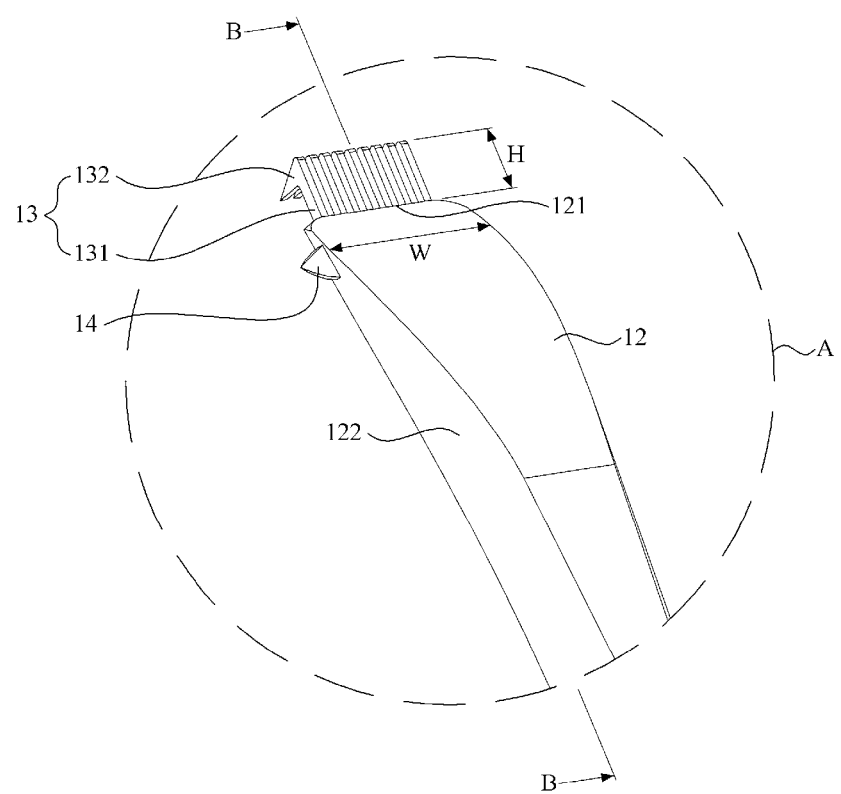
FIG. 6 is an enlarged view of area A of FIG. 5.

Refer now to FIG. 5 and FIG. 6; where FIG. 5 is a schematic perspective view of a preferred periosteal elevator having a hook-shaped comblike structure in accordance with the present invention, and FIG. 6 is an enlarged view of area A of FIG. 5. As shown, the preferred periosteal elevator having a hook-shaped comblike structure 1 for combing and elongating subcutaneous fibrous tissues 21a and 21b (see FIG. 8) includes a stem bar 11, a first spoon end 12 and a plurality of hook-shaped comblike structures 13.

The stem bar 11 has a first end portion P1 and a second end portion P2 opposing to the first end portion P1. In this preferred embodiment, the stem bar 11 further has a hand-gripped portion 111 for a user (generally, a dentist) to manipulate. The hand-gripped portion 111 can be made of a slip-proof material such as rubber, so that, while in use, manipulation of the periosteal elevator 1 won't be affected by patient's breath and/or user's hand sweat. The stem bar 11 can be, but not limited to, a round pillar or a polygonal column, with a predetermined length for the dentist able to comb and elongate any subcutaneous fiber in the mouth.

The first spoon end 12, fixed or formed at the first end portion P1 of the stem bar 11, has a spoon-end edge 121 and a spoon-end lateral side 122. In this preferred embodiment, the spoon-end edge 121 is a straight edge, and the first spoon end 12 has a spoon-end width W. In considering the size of wound in the operation, the spoon-end width W is within a range of 3 mm and 15 mm, by which additional hurt to the subcutaneous fibrous tissues 21a and 21b would be hard to make.

The plurality of hook-shaped comblike structures 13 (only one labeled in the figure) are preferably arranged parallel to each other by a predetermined spacing at the spoon-end edge 121, and each of the hook-shaped comblike structures 13 has an extension portion 131 and a hook-like comb portion 132. The extension portion 131 is extended against the stem bar 11 from the spoon-end edge 121. On the other hand, the hook-like comb portion 132 is extended from the extension portion 131. In this preferred embodiment, the hook-shaped comblike structures 13 can be integrated as a unique piece with the spoon-end edge 121, and the hook-like comb portion 132 can be also integrated with the extension portion 131 as a unique piece. In some other embodiments of the present invention, the hook-shaped comblike structures 13 can be fixed to the spoon-end edge 121 by other means, and also the hook-like comb portion 132 can also be fixed to the extension portion 131 by other means.

In considering the size of wound and practical operational convenience, the hook-shaped comblike structure 13 further has a protrusive height H, preferably within a range of 0.8 mm and 1 mm. In addition, the neighboring hook-shaped comblike structures are spaced by a predetermined spacing, so that an integral object resembled to a comb is produced to provide a better performance in combing and elongating subcutaneous fiber.

In the preferred embodiment, the periosteal elevator having a hook-shaped comblike structure 1 further includes a knife protrusion 14 and a second spoon end 15. The knife protrusion 14 is fixed to the spoon-end lateral side 122 of the first spoon end 12 to perform cutting. The second spoon end 15 is fixed to the second end portion P2 of the stem bar 11.

Figure 7:
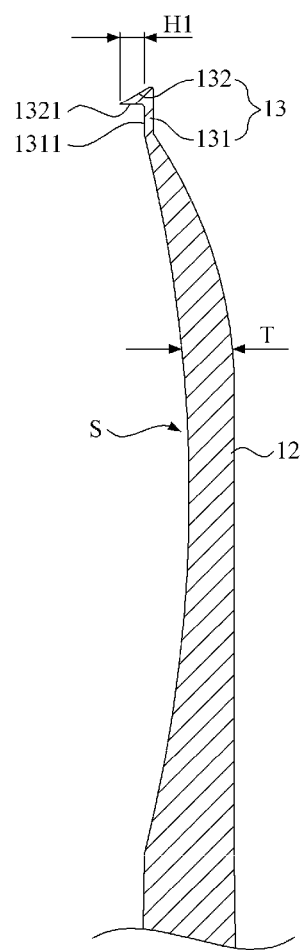
FIG. 7 is a schematic cross-sectional view of FIG. 6 along line B-B.

Referring now to FIG. 7, a schematic cross-sectional view of FIG. 6 along line B-B is shown. The first spoon end 12 is furnished with a filler-accommodating space S for containing a filler, generally the bone grafts. In addition, in considering the width and toughness of the subcutaneous fibrous tissues 21a and 21b in ordinary people, a spoon-end thickness T of the first spoon end 12 is preferably within a range of 1 mm and 2 mm, so that additional cuts could be avoided in the subcutaneous fibrous tissues 21a, 21b.

It shall explain particularly that, in the preferred hook-shaped comblike structure 13, the hook-like comb portion 132 has a comb surface 1321, and the extension portion 131 has an inner-side extension surface 1311, in which the comb surface 1321 and the inner-side extension surface 1311 are together to form an angle having a range of 60-100 degrees. In this preferred embodiment, the angle is 90 degrees, by which a better combing and elongating performance for subcutaneous fiber can be achieved. As shown, the comb surface 1321 has a comb-tooth length H1. In considering the width of the subcutaneous fibrous tissue 21a or 21b, the comb-tooth length H1 is preferably within a range of 0.1 mm and 0.3 mm, by which a better combing and elongating performance for subcutaneous fiber can be achieved. Since the comb-tooth length H1 of the comb surface 1321 is equal to an accessible depth of the comblike structure into the subcutaneous fibrous tissue 21a or 21b, thus the periosteal elevator having a hook-shaped comblike structure 1 provided by the present invention can prevent the comblike structure from having an excessive comb-tooth length H1 that might lead to additional cuts caused by combing deep too much into the subcutaneous fibrous tissues 21a and/or 21b, and also from having an insufficient comb-tooth length H1 that might lead to a poor tension performance caused by combing only at the surface layers of the subcutaneous fibrous tissues 21a and/or 21b.

Figure 8:
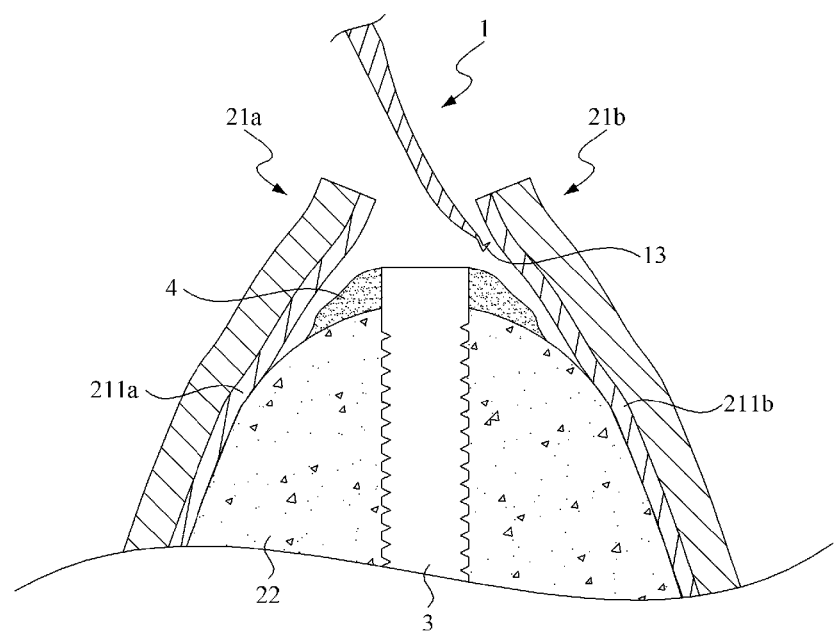
FIG. 8 is a schematic cross-sectional view of an alveolar bone implanted with a dental implant and with a subcutaneous fibrous tissue thereof to be combed and elongated by the periosteal elevator having a hook-shaped comblike structure of FIG. 5.
Figure 8A:
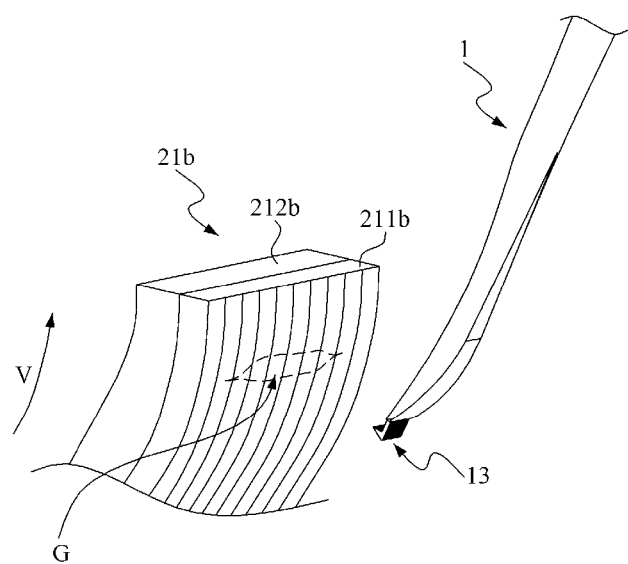
FIG. 8A is an enlarged view showing the periosteal elevator having a hook-shaped comblike structure of FIG. 5 and the subcutaneous fibrous tissue to be combed and elongated.

Refer now to FIG. 8 and FIG. 8A; where FIG. 8 is a schematic cross-sectional view of an alveolar bone implanted with a dental implant and with a subcutaneous fibrous tissue thereof to be combed and elongated by the periosteal elevator having a hook-shaped comblike structure of FIG. 5, and FIG. 8A is an enlarged view showing the periosteal elevator having a hook-shaped comblike structure of FIG. 5 and the subcutaneous fibrous tissue to be combed and elongated. As shown, in this stage, the dentist has already embedded a dental implant 3 into an alveolar bone 22, and filled the bone grafts 4 to cover the alveolar bone 22. Then, a suturing operation can be performed.

The dentist can apply the periosteal elevator having a hook-shaped comblike structure 1 provided by the present invention to comb and elongate the subcutaneous fibrous tissues 21a and 21b. In details, the subcutaneous fibrous tissue 21a includes a periosteum 211a and a muscle fiber 212a (see FIG. 9). Similarly, the subcutaneous fibrous tissue 21b also includes a periosteum 211b and a muscle fiber 212b. The dentist uses the knife protrusion 14 to make a cut G at the periosteum 211b, and applies the hook-shaped comblike structures 13 to comb the muscle fiber 212b in a texture direction V. While in combing, the muscle fiber 212b is also stretched simultaneously. Since the muscle fiber 212b connects the periosteum 211b and the dermis (not shown in the figure), so the periosteum 211b and the dermis would be stretched with the muscle fiber 212ba as well. In combing and elongating the muscle fiber 212b, if a tendon (not shown in the figure, and extending not parallel to the texture direction) is combed, then the combing and elongating would be obstructed. At this time, the dentist can apply the knife protrusion 14 to break the tendon, such that the combing andelongating process can be smooth again. In some other embodiments of the present invention, the dentist can use the hook-shaped comblike structures 13 to comb and elongate the periosteum 211b directly.

No matter what kind of the combing and elongating process is applied, the hook-shaped comblike structures 13 can always comb and elongate the subcutaneous fibrous tissues 21a and 21b effectively. Though only the subcutaneous fibrous tissue 21b is shown to be combed and elongated in the figure, yet a similar combing and elongating process can be applied only to the subcutaneous fibrous tissue 21a, or to both the subcutaneous fibrous tissues 21a and 21b. Since the combing and elongating process can hurt the subcutaneous fibrous tissues 21a and 21b slightly, thus only limited breeding may be encountered. Consequently, the healing of the wound and/or the postoperative recovery won't be significantly affected.

Figure 9:
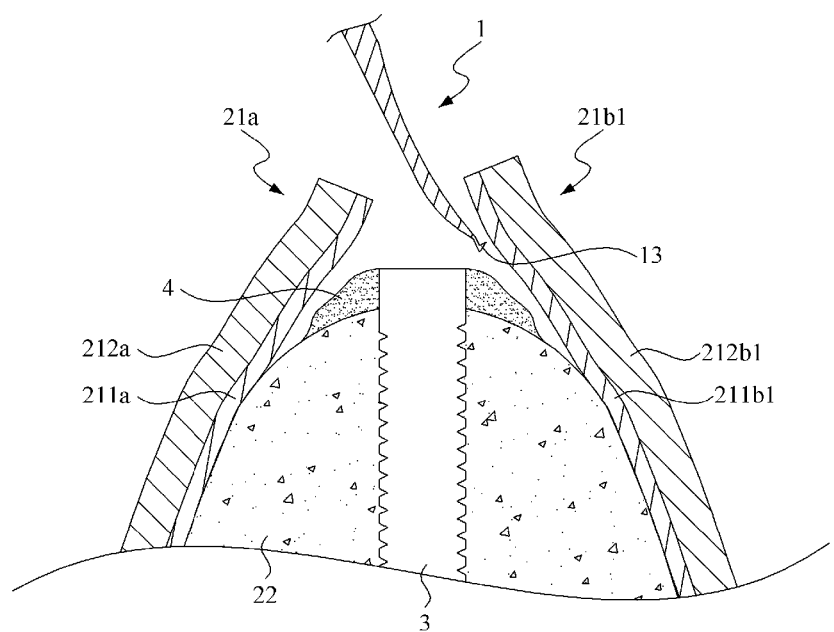
FIG. 9 demonstrates another state of FIG. 8, with the subcutaneous fibrous tissue been combed and elongated by the periosteal elevator having a hook-shaped comblike structure of FIG. 5.
Figure 10:
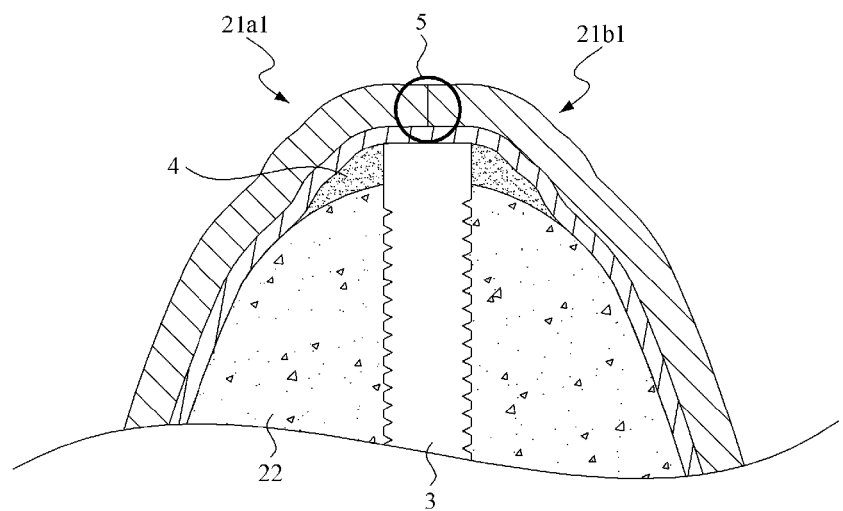
FIG. 10 demonstrates a further state of FIG. 9 with the wound been sutured.

Then, refer to both FIG. 9 and FIG. 10; where FIG. 9 demonstrates another state of FIG. 8, with the subcutaneous fibrous tissue been combed and elongated by the periosteal elevator having a hook-shaped comblike structure of FIG. 5, and FIG. 10 demonstrates a further state of FIG. 9 with the wound been sutured.

As shown, after the subcutaneous fibrous tissue 21b (labeled in FIG. 8 and FIG. 8A) is combed and elongated by the periosteal elevator having a hook-shaped comblike structure 1, the subcutaneous fibrous tissue 21b would be stretched to become longer, and thus the stretched subcutaneous fibrous tissue herein is labeled as 21b1. In details, since the muscle fibrous tissue 212b (see FIG. 8 and FIG. 8A) is combed and elongated to elongate the muscle fibrous tissue 212b1, so the periosteum 211b (see FIG. 8 and FIG. 8A) would be stretched to become the periosteum 211b1. Thus, the subcutaneous fibrous tissue 21b including the muscle fibrous tissue 212b and the periosteum 211b would be stretched simultaneously to become the subcutaneous fibrous tissue 21b1. After the dentist uses the periosteal elevator having a hook-shaped comblike structure 1 to comb and elongate the subcutaneous fibrous tissue 21b to become the subcutaneous fibrous tissue 21b1, the same combing and elongating process can be applied to stretch the subcutaneous fibrous tissue 21a, such that the subcutaneous fibrous tissue 21a can be combed and elongated to become the subcutaneous fibrous tissue 21a1. Accordingly, the subcutaneous fibrous tissues 21a1 and 21b1 can be thus sutured after the alveolar bone 22 is implanted by the dental implant 3 and filled by the bone grafts 4. Hence, the dentist can easily suture the subcutaneous fibrous tissues 21a1 and 21b1 together by a stitch 5.

In addition, prior to the aforesaid process, the dentist can use the knife protrusion 14 to cut and separate the subcutaneous fibrous tissues 21a and 21b over the alveolar bone 22, and use the second spoon end 15 to open the subcutaneous fibrous tissues 21a and 21b so as to expose the alveolar bone 22, so that the dentist can implant the dental implant 3 into the alveolar bone 22. After the dentist implants the dental implant 3, the filler-accommodating space S of the first spoon end 12 can be used to contain the bone grafts 4, and then the bone grafts 4 are fed to the alveolar bone 22 and the dental implant 3. Hence, the periosteal elevator having a hook-shaped comblike structure 1 of the present invention can provide multi-functions. With the periosteal elevator having a hook-shaped comblike structure 1 of the present invention, the dentist needn't to change cutting tools frequently in a dental surgery. Thereupon, the usage convenience can be improved, and time for the surgery can be shortened.

In the art, a plurality of cuts are needed at the inner side of the subcutaneous fibrous tissue, and the number and depth of the cuts would affect the stretchable length of the subcutaneous fibrous tissue. Though more cuts or deeper cuts may increase the stretchable length of the subcutaneous fibrous tissue, yet the possibility of additional wounds to the subcutaneous fibrous tissue would be raised as well. Under such a circumstance, further swelling and/or contaminations at the wounds might be inevitable, and the postoperative recovery of the patient would be prolonged definitely. However, by providing the periosteal elevator having a hook-shaped comblike structure of the present invention, a combing and elongating process upon muscle fibers or periostea can be performed with or without a cut, and the subcutaneous fibrous tissue can be stretched through combing and elongating the muscle fiber or the periosteum.

In addition, by providing the periosteal elevator having a hook-shaped comblike structure of the present invention, the periosteum can be easily separated from the alveolar bone, the subcutaneous fibrous tissue can be combed and elongated conveniently, the bone grafts can be filled simultaneously, the subcutaneous fibrous tissue can be cut, and the tendon extending in a different texture direction can be broken as well. In comparison with the conventional tool that can provide only a mono function, the periosteal elevator having a hook-shaped comblike structure of the present invention can provide multi-functions. With the periosteal elevator having a hook-shaped comblike structure of the present invention at hand, the dentist needn't to change cutting tools frequently in a dental surgery, and thus time for the surgery can be significantly shortened.

While the present invention has been particularly shown and described with reference to a preferred embodiment, it will be understood by those skilled in the art that various changes in form and detail may be without departing from the spirit and scope of the present invention.

What is claimed is:

1. A periosteal elevator having a hook-shaped comblike structure, adapted to be applied to comb and elongate a subcutaneous fibrous tissue, comprising:
   a stem bar;
   a first spoon end, fixed to a first end portion of the stem bar, further having a spoon-end edge; and
   a plurality of hook-shaped comblike structures, separated from each other, fixed to the spoon-end edge, each of the plurality of hook-shaped comblike structures having an extension portion and a hook-like comb portion, the extension portion being extended from the spoon-end edge, the hook-like comb portion being extended further from the extension portion, the plurality of hook-shaped comblike structures being applied to comb and elongate the subcutaneous fibrous tissue upon when the subcutaneous fibrous tissue is cut and separated from a bone tissue;
   wherein a comb surface of the hook-like comb portion and an inner-side extension surface of the extension portion are together to form an angle within a range of 60 and 100 degrees.

2. The periosteal elevator having a hook-shaped comblike structure of claim 1, further including a knife protrusion fixed to a spoon-end lateral side of the first spoon end.

3. The periosteal elevator having a hook-shaped comblike structure of claim 1, further including a second spoon end connected with a second end portion of the stem bar by opposing to the first end portion, the second spoon end being to tear the subcutaneous fibrous tissue off the bone tissue.

4. The periosteal elevator having a hook-shaped comblike structure of claim 1, wherein the stem bar further has a hand-gripped portion.

5. The periosteal elevator having a hook-shaped comblike structure of claim 1, wherein the spoon-end edge is one of an arc edge and a straight edge.

6. The periosteal elevator having a hook-shaped comblike structure of claim 1, wherein the first spoon end has a spoon-end width within a range of 3 mm and 15 mm.

7. The periosteal elevator having a hook-shaped comblike structure of claim 1, wherein the plurality of hook-shaped comblike structures have a protrusive height within a range of 0.8 mm and 1 mm.

8. The periosteal elevator having a hook-shaped comblike structure of claim 1, wherein the first spoon end has a spoon-end thickness within a range of 1 mm and 2 mm.

9. The periosteal elevator having a hook-shaped comblike structure of claim 1, wherein the comb surface of the plurality of hook-shaped comblike structures has a comb-tooth length within a range of 0.1 mm and 0.3 mm.

* * * * *